United States Patent
Sasaki

(10) Patent No.: US 8,092,399 B2
(45) Date of Patent: Jan. 10, 2012

(54) SLEEP STATE MEASURING APPARATUS AND SLEEP STATE MEASURING METHOD

(75) Inventor: Toshiaki Sasaki, Tokyo (JP)

(73) Assignee: Tanita Corporation, Tokyo (JP)

( * ) Notice: Subject to any disclaimer, the term of this patent is extended or adjusted under 35 U.S.C. 154(b) by 429 days.

(21) Appl. No.: 12/222,828

(22) Filed: Aug. 18, 2008

(65) Prior Publication Data
US 2009/0051550 A1    Feb. 26, 2009

(30) Foreign Application Priority Data
Aug. 24, 2007 (JP) ................................ 2007-218823

(51) Int. Cl.
*A61B 5/103* (2006.01)
*A61B 5/117* (2006.01)

(52) U.S. Cl. ........................................ 600/595; 600/587

(58) Field of Classification Search ................... 340/575; 600/484, 500, 502, 529, 534, 575, 587, 595
See application file for complete search history.

(56) References Cited

U.S. PATENT DOCUMENTS

| | | | |
|---|---|---|---|
| 4,299,233 A * | 11/1981 | Lemelson | 600/500 |
| 5,796,340 A * | 8/1998 | Miller | 340/573.7 |
| 6,450,957 B1 * | 9/2002 | Yoshimi et al. | 600/309 |
| 2002/0007124 A1 * | 1/2002 | Woodward | 600/481 |
| 2006/0042409 A1 | 3/2006 | Nemoto | |
| 2006/0129047 A1 * | 6/2006 | Ruotoistenmaki | 600/483 |
| 2006/0169282 A1 | 8/2006 | Izumi | |

FOREIGN PATENT DOCUMENTS

| | | |
|---|---|---|
| JP | 2000-271103 | 10/2000 |
| JP | 2004-113329 | 4/2004 |
| JP | 2004-113618 | 4/2004 |
| WO | WO 2005/082252 | 9/2005 |

* cited by examiner

*Primary Examiner* — Max Hlndenburg
*Assistant Examiner* — Charles Becker
(74) *Attorney, Agent, or Firm* — Edwards Neils PLLC; Paul F. Neils, Esq.

(57) ABSTRACT

Even if a mattress or the like suffers long-term deterioration, a sleep state measuring apparatus is provided which can set a suitable amplification factor A of a biosignal. The sleep state measuring apparatus detects the biosignal which changes depending on the sleep state of a person who gets on the mattress filled with water, amplifies the biosignal, and estimates the sleep state based on the biosignal. A static component P of the mattress internal pressure detected by a biosignal sensor is first obtained (S 11). The mattress internal pressure is the pressure of water in the mattress. From the static component P of the mattress internal pressure, a fluctuation part $\Delta V$ of the mattress internal pressure depending on the value is specified (S 12). Each value of the fluctuation part $\Delta V$ of the mattress internal pressure is obtained beforehand by applying a predetermined load, and changing the static component P of the mattress internal pressure. The above-described amplification factor A is calculated by correcting predetermined standard amplification factor $A_0$ with the specified fluctuation part $\Delta V$ (S 13).

8 Claims, 11 Drawing Sheets

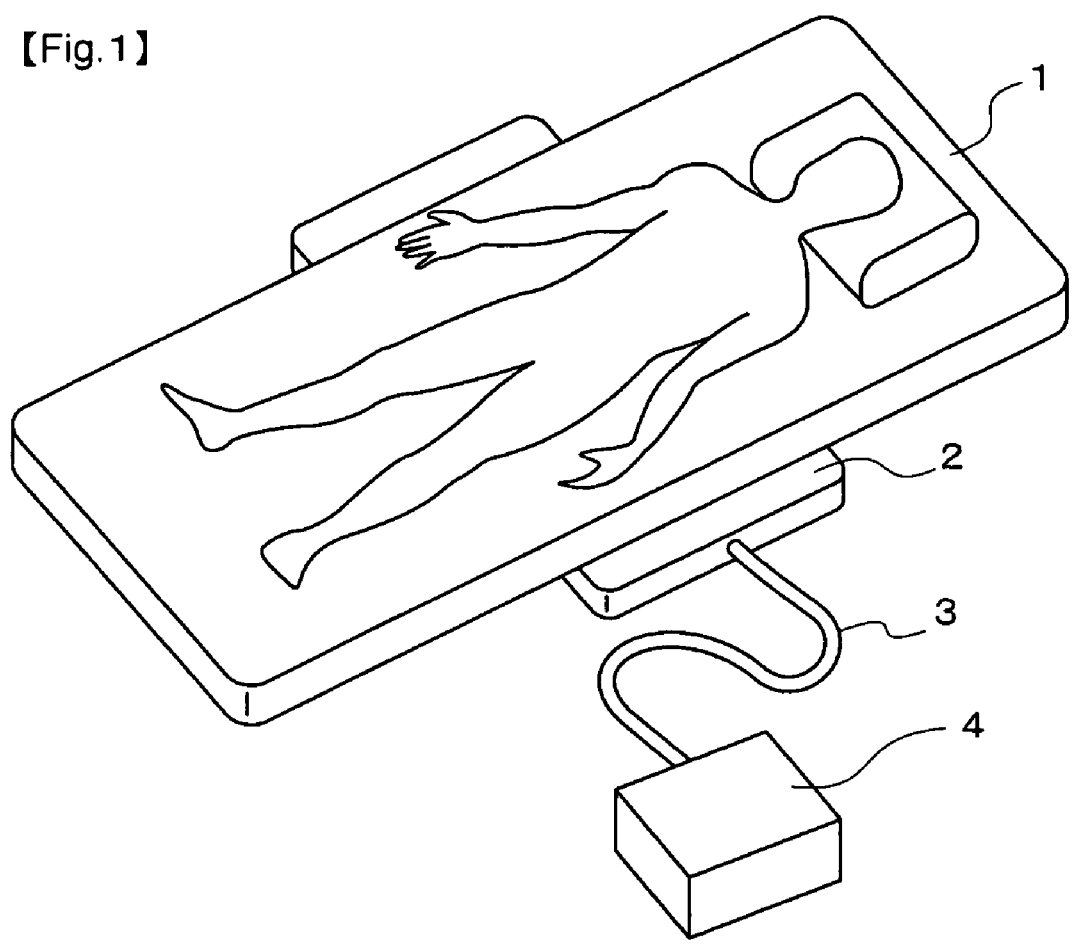
[Fig. 1]

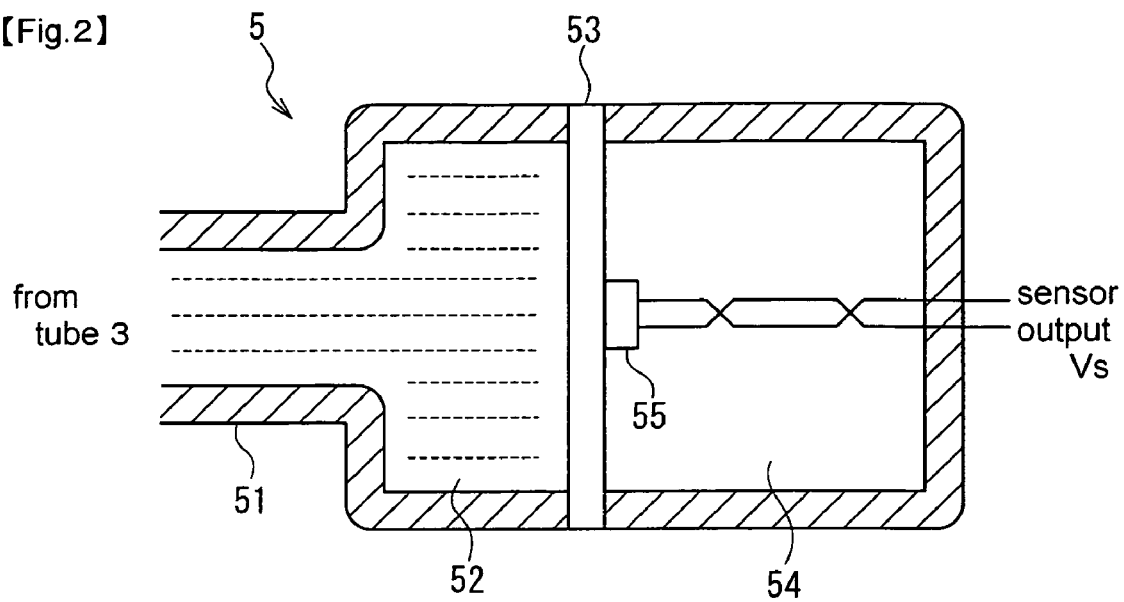
[Fig.2]

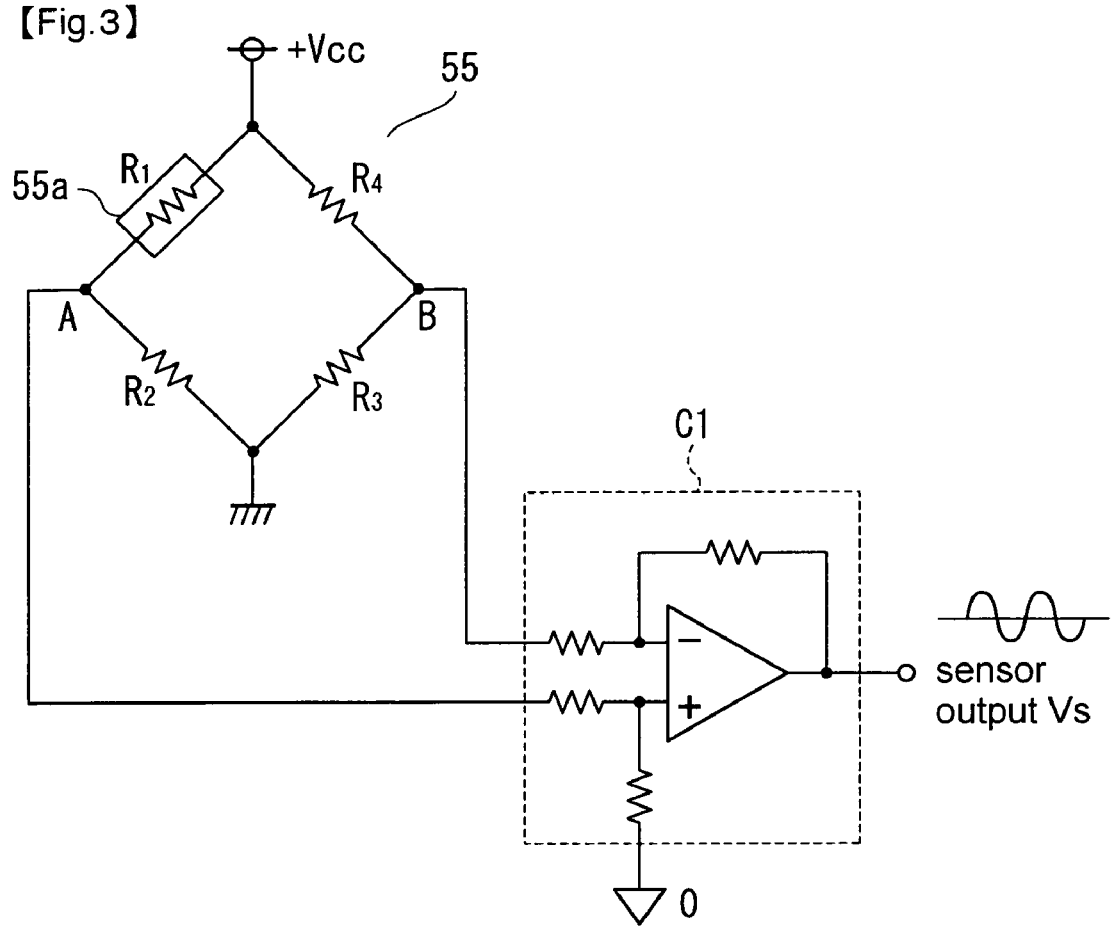
[Fig.3]

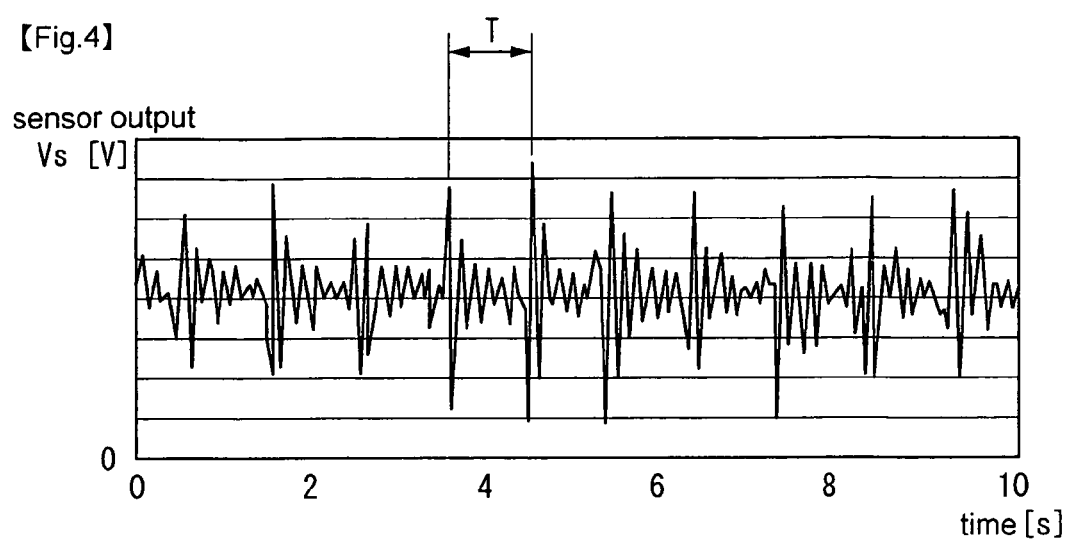

[Fig.5]
(a)
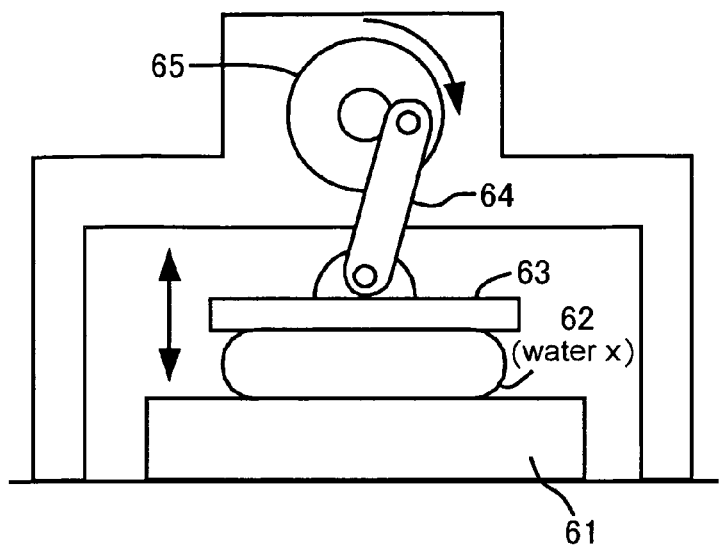
(b)
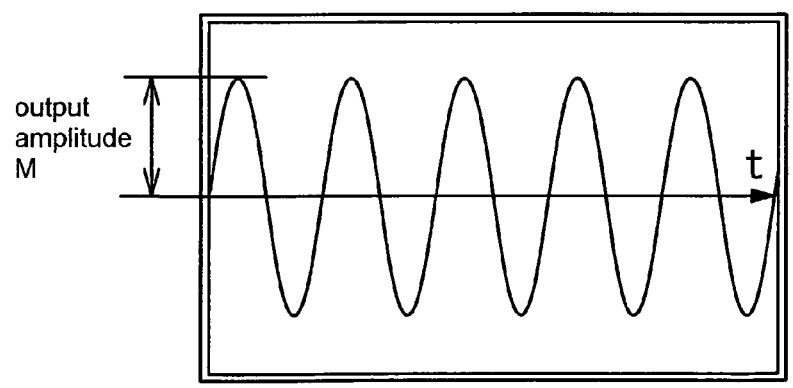

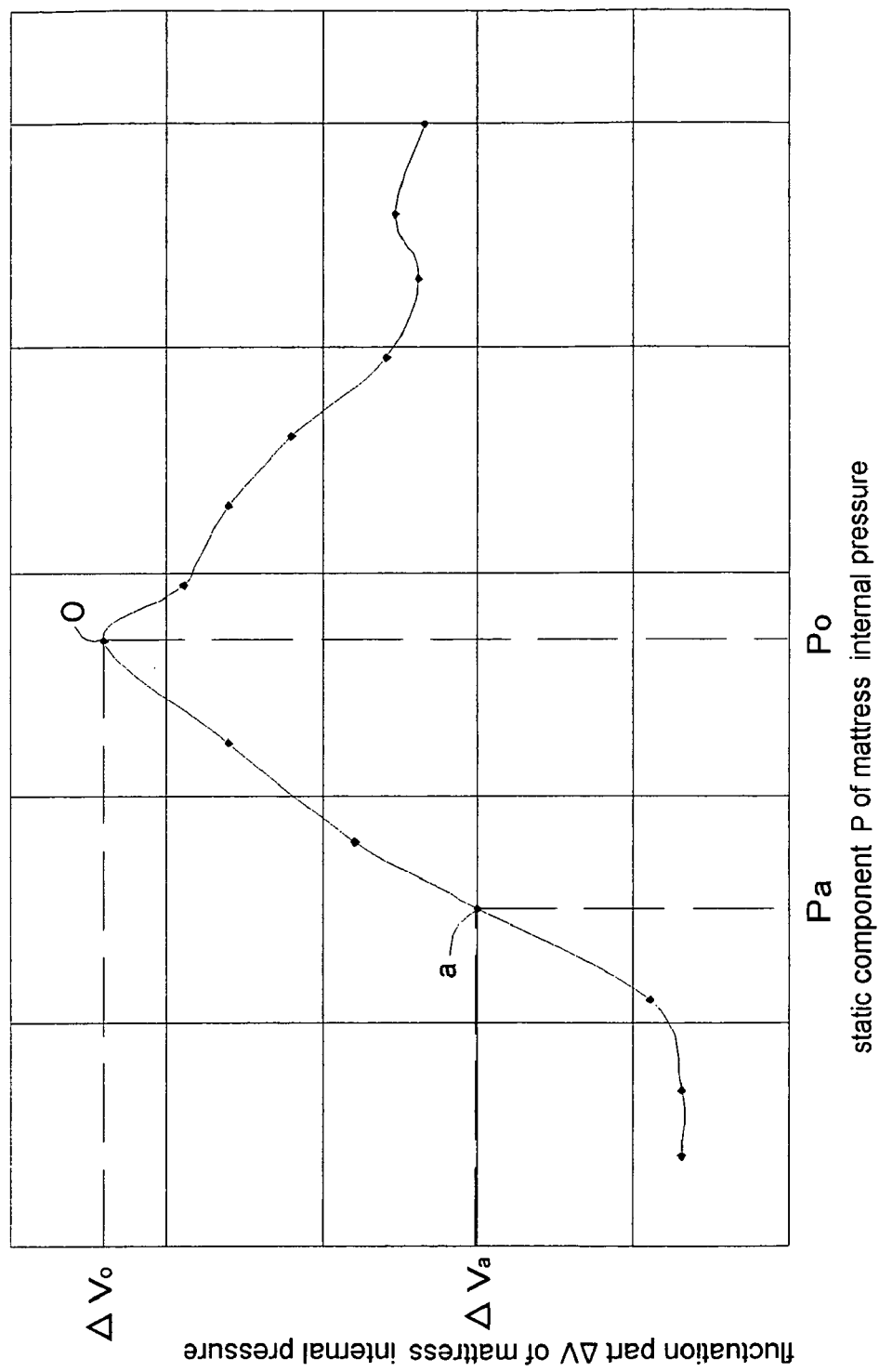
[Fig.6]

[Fig. 7]
(a) 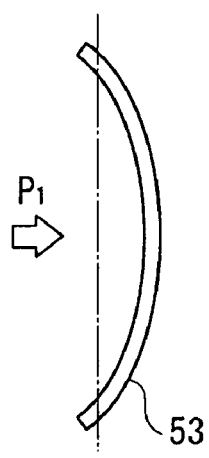
(b) 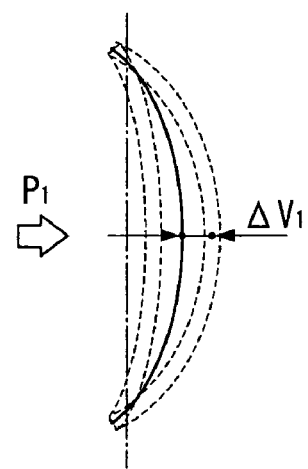

[Fig.8]
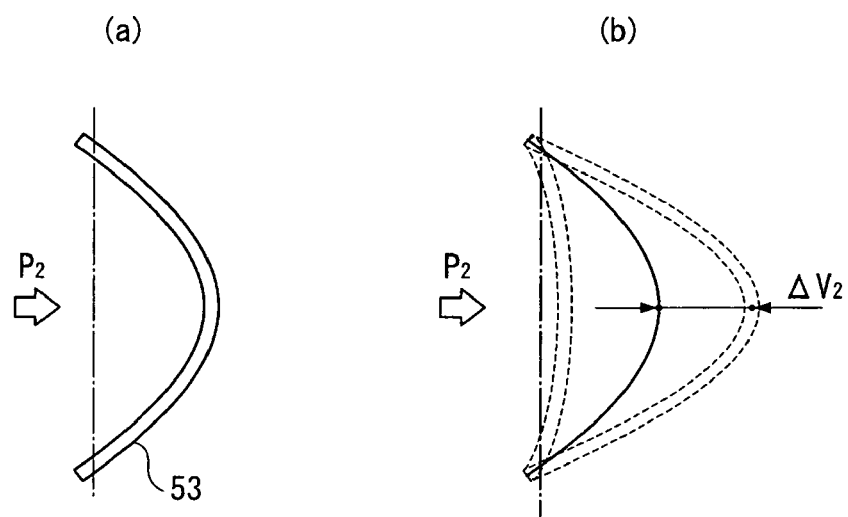

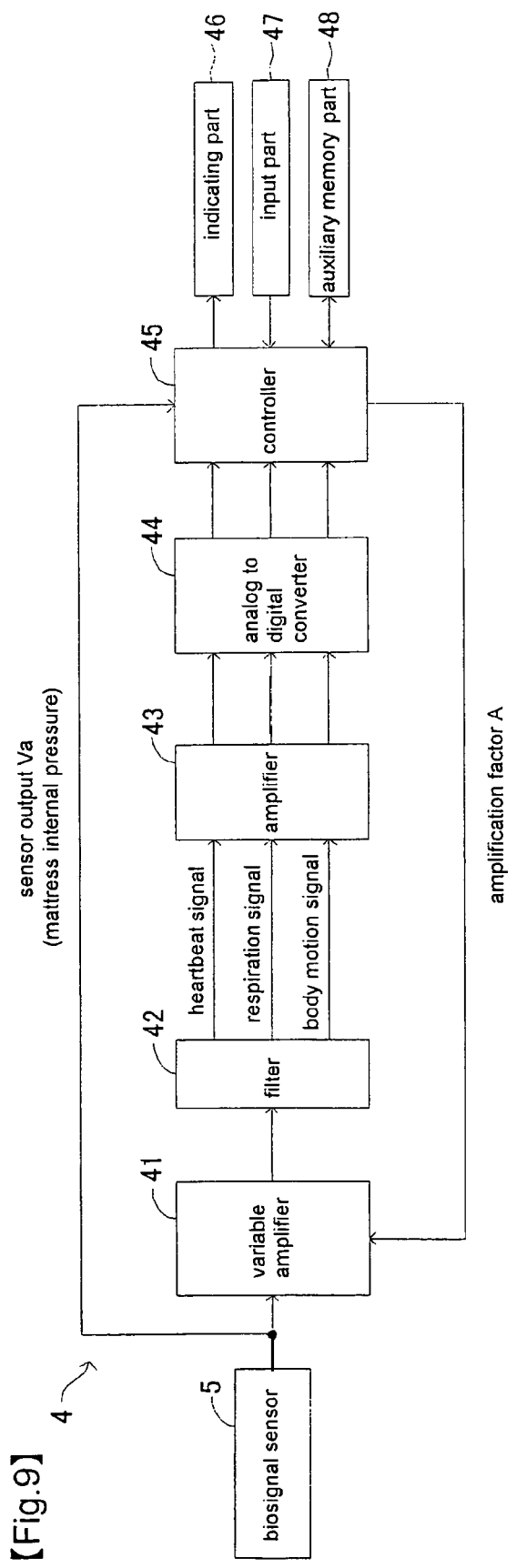

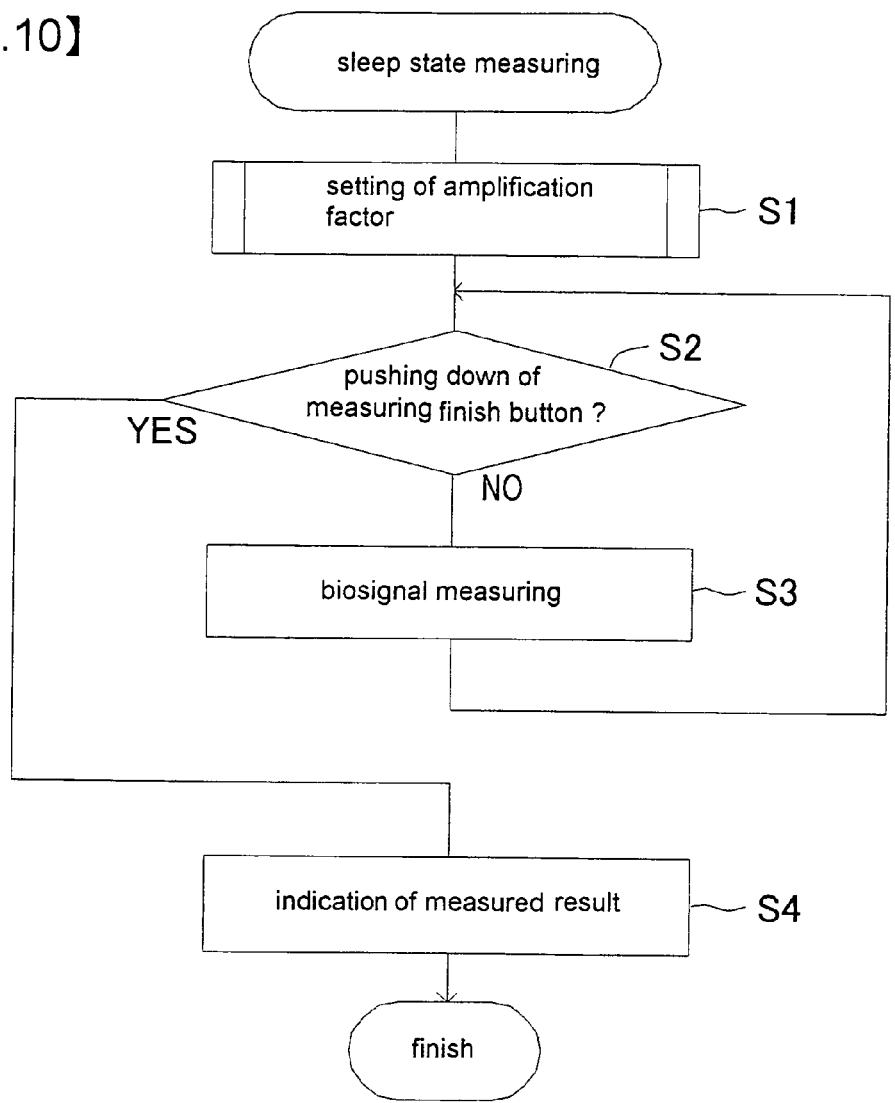
[Fig.10]

[Fig.11]
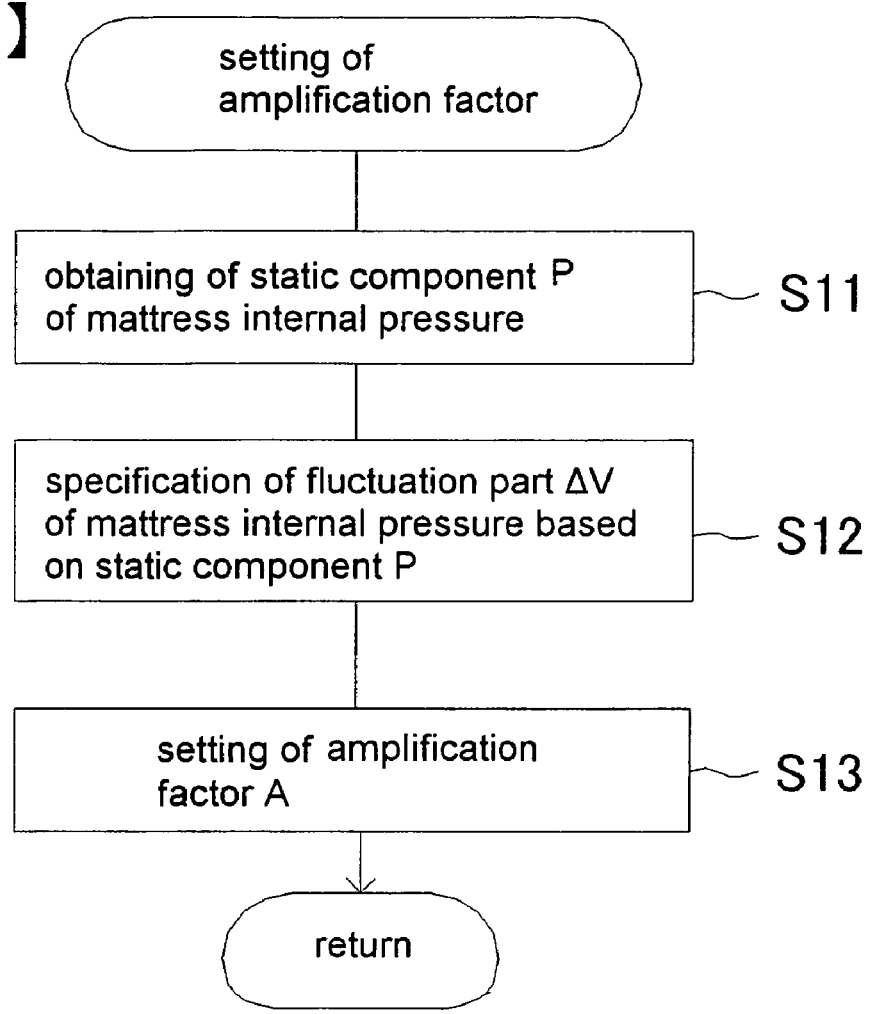

SLEEP STATE MEASURING APPARATUS AND SLEEP STATE MEASURING METHOD

CROSS REFERENCE OF THE INVENTION

The present application claims benefit of the filing date of Japanese Patent Application No. 2007-218823 filed Aug. 24, 2007, and the contents of which are herein incorporated by reference in their entirety.

BACKGROUND OF THE INVENTION

1. Field of the Invention

The present invention relates to a sleep state measuring apparatus and a sleep state measuring method for detecting a biosignal which changes depending on the sleep state of a living body that gets on a mattress filled with fluid, amplifying, and estimating the sleep state based on the amplified biosignal.

2. Description of the Related Art

One of this kind of already-known apnea detecting apparatus detects the apnea in a user's sleep state, and the apnea detecting apparatus is equipped with the automatic gain control unit. In this apnea detecting apparatus, the pressure fluctuation which is propagated to the inside of an air mattress is detected from the user's body lying down on the air mattress filled with air as the biosignal by a microdifferential pressure sensor. The automatic gain control unit automatically controls the gain (amplification factor) of the detected biosignal and outputs the amplified biosignal to a filter equipped at the latter step (refer to Patent Document 1).

This filter is adjusted to heartbeat or respiration, for example. The filter adjusted to heartbeat extracts heartbeat signals and the filter adjusted to respiration extracts respiration signals. In addition, it is estimated whether the user on the mattress is in a particular sleep stage, or whether the user is in the apneic condition, by the latter procedure, from the fluctuation pattern of these heartbeat signals and respiration signals.

[Patent Document 1]

Japanese Unexamined Patent Application Publication No. 2000-271103 (Paragraph number [0017], [0020] to [0022], FIG. 1 and others).

BRIEF SUMMARY OF THE INVENTION

However, in the conventional automatic gain control unit mentioned above, the gain control could not always be carried out appropriately. That is, the signal of a frequency band which is necessary for the latter procedure of the detected biosignal corresponds to the heartbeat, the respiration, or the like. However, since the user changes sides or goes to the bathroom during sleeping hours, the signals by other body motion other than the heartbeat and the respiration work as a disturbance in the biosignals, so that the gain can be automatically adjusted in response to these disturbances.

Also, it is confirmed that the pressure in the mattress is obtained by superposing the static component on the dynamic component (the fluctuation part of the mattress internal pressure), and that the size of the static component of the mattress internal pressure influences the size of the dynamic component. The static component of this mattress internal pressure is based on the pressure of the fluid in the mattress at the time of production, the weight of the human body, or the like, and the dynamic component of the mattress internal pressure is based on the vibration of the human body such as the heartbeat, the respiration, or the like.

Here, since the mattress comprises synthetic resins such as polyvinyl chloride or the like, when this mattress is expanded by long-term deterioration or the like and the content of the mattress is decreased, the static component of the mattress internal pressure becomes smaller gradually. Therefore, the decrease of this mattress internal pressure also brings about a cause which makes the fluctuation width of the biosignal small. In the conventional automatic gain control unit, regardless of the causes, since the gain is controlled from the size of the biosignal value after amplification, there is a possibility that the analysis of the biosignal cannot be appropriately carried out by the control of this gain.

SUMMARY OF THE INVENTION

The purpose of the present invention is to provide the sleep state measuring apparatus and the sleep state measuring method which can solve these problems.

The sleep state measuring apparatus according to the present disclosure detects the biosignal which changes depending on the sleep state of the living body from this living body that gets on the mattress filled with fluid, amplifies the biosignal, and estimates the sleep state based on the amplified biosignal. This sleep state measuring apparatus is equipped with a detector, a specifier, and a calculator. The detector detects the static component P of the mattress internal pressure which is the pressure of the fluid in the mattress. The specifier specifies the fluctuation part $\Delta V$ of the mattress internal pressure at the time of applying predetermined load which changes depending on the value of the static component P from the static component P detected by the detector. The calculator calculates amplification factor A used for the amplification of the biosignal by correcting predetermined standard amplification factor $A_0$ with the fluctuation part $\Delta V$ specified by the specifier.

According to another aspect of the invention, the sleep state measuring apparatus is equipped with the memory part which memorizes the reference table showing the correspondence relation between the static component P of the mattress internal pressure and the fluctuation part $\Delta V$ of the mattress internal pressure. In this case, the specifier obtains the fluctuation part $\Delta V$ depending on the static component P detected by the detector from the reference table memorized in this memory part.

According to a further aspect of the invention, the calculator first finds the correction factor by dividing the standard fluctuation part $\Delta V_0$ which is the fluctuation part of the mattress internal pressure corresponding to the standard amplification factor $A_0$ with the fluctuation part $A\Delta$ specified by the specifier, and then calculates the amplification factor A by multiplying the found correction factor to the standard amplification factor $A_0$.

According to a further aspect of the invention, the detector detects the detected value in the state where the living body does not get on the mattress, as the static component P of the mattress internal pressure.

According to a further aspect of the invention, the apparatus is equipped with a low pass filter which transmits the low frequency band of the biosignal pass. In this case, the detector detects the biosignal which passed the low pass filter in the state where the living body gets on the mattress, as the static component P of the mattress internal pressure.

According to a further aspect of the invention, the detector calculates first average biosignal value in the state where the living body gets on the mattress, and then detects the calculated average value as the static component P of the mattress internal pressure.

According to a further aspect of the invention, the detector detects the mattress internal pressure fluctuating in the state where the living body gets on the mattress, as the biosignal.

According to an additional aspect of the invention, the detector has a fluid chamber, an air chamber, a pressure receiving membrane, and a strain gauge. The fluid chamber is connected with the mattress and the fluid chamber is filled with fluid. The air chamber is filled with air. The pressure receiving membrane separates the air chamber from the fluid chamber. The strain gauge is set on the pressure receiving membrane, and the strain gauge detects the fluctuation of the pressure of the fluid in the fluid chamber.

According to another aspect of the invention, the sleep state measuring method detects the biosignal which changes depending on the sleep state of the living body in the state where the living body gets on the mattress filled with fluid, amplifies the biosignal, and estimates the sleep state based on the amplified biosignal. The sleep state measuring method comprises (1) detecting the static component P of the mattress internal pressure which is the pressure of the fluid in the mattress, (2) specifying the fluctuation part $\Delta V$ of the mattress internal pressure at the time of applying the predetermined load which changes depending on the value of the detected static component P from the static component P detected, and (3) correcting the predetermined standard amplification factor $A_0$ using the specified fluctuation part $\Delta V$, and calculates the amplification factor A used for the amplification of the biosignal.

EFFECTS OF THE INVENTION

According to the present invention, the size $\Delta V$ of the fluctuation part (dynamic component) of the mattress internal pressure depending on the value is specified from the value of the static component P of the detected mattress internal pressure. And the amplification factor A of the biosignal is set by the correcting predetermined standard amplification factor $A_0$ based on the fluctuation part $\Delta V$. Therefore, even if the mattress or the like is long-term deteriorated, the suitable amplification factor of the biosignal can be set easily.

BRIEF DESCRIPTION OF THE DRAWINGS

FIG. 1 shows a whole composition of the sleep state measuring apparatus which is one of the embodiments of the invention.

FIG. 2 shows a composition of the biosignal sensor.

FIG. 3 shows an electric circuit diagram showing an example of the pressure fluctuation detecting part in the biosignal sensor.

FIG. 4 shows an example of the biosignal (sensor output).

FIG. 5 shows an outline composition of the experimental apparatus for obtaining the relation between the static component P of the mattress internal pressure and the fluctuation part $\Delta V$ of the mattress internal pressure.

FIG. 6 shows a graph showing the correspondence relation between the static component P of the mattress internal pressure and the fluctuation part $\Delta V$ of the mattress internal pressure.

FIG. 7 shows a first schematic view for explaining the influence on the fluctuation part $\Delta V$ by the static component P of the mattress internal pressure.

FIG. 8 shows a second schematic view for explaining the influence on the fluctuation part $\Delta V$ by the static component P of the mattress internal pressure.

FIG. 9 shows a block diagram showing the outline of the composition of the main part of the sleep state measuring apparatus.

FIG. 10 shows a flow chart showing the outline of the sleep state measuring process.

FIG. 11 shows a flow chart showing the flow of the amplification factor setting process of S1 shown in FIG. 10.

DESCRIPTION OF THE PREFERRED EMBODIMENTS

Hereafter, the embodiment related to the present invention is explained in detail, referring to the drawings.

Best Mode For Carrying Out The Invention

Concerning the best embodiment of the present invention, the whole composition about the sleep state measuring apparatus is first explained. The sleep state measuring apparatus detects the biosignal which changes depending on the user's (living body's) sleep state, amplifies the biosignal, and estimates the user's sleep state based on the amplified biosignal.

As shown in FIG. 1, the sleep state measuring apparatus is used with the bedding 1, and the apparatus is equipped with the mattress 2, the tube 3, and the main part 4 of the sleep state measuring apparatus.

The user who is the objective of the sleep state measurement lies down on the bedding 1 and the mattress 2 is laid under the bedding 1. One end of the tube 3 is connected to the mattress 2 and the other end is connected to the biosignal sensor 5 attached to the main part 4 of the sleep state measuring apparatus. The mattress 2 and the tube 3 are filled with water (example of the fluid, and also air or the like can be used). Hereby, the heartbeat (pulse), the respiration, and the vibration by other body motion which are generated from the user's body on the bedding 1 are transmitted as the change of the mattress internal pressure (the pressure of the water in the mattress) through the mattress 2 and the tube 3 to the biosignal sensor 5 in the main part 4 of the sleep state measuring apparatus 4.

Here, since the mattress 2 is laid under the bedding 1, and the user gets on the mattress 2 indirectly. However, the user can also lie down on the mattress 2 directly as well in the case where the mattress 2 is laid over the bedding 1. Also, the mattress 2 may be laid on the upper part or the bottom part of a pillow, or can be formed as a shape of the pillow.

The biosignal sensor 5 of the main part 4 of the sleep state measuring apparatus detects the mattress internal pressure. The detected mattress internal pressure is approximately constant in the state where the user does not get on, and the mattress internal pressure is used for setting the amplification factor of the variable amplifier in the main part 4 of the sleep state measuring apparatus at the time of starting the sleep state measuring. Herewith, the mattress internal pressure fluctuating in the state where the user gets on the mattress 2 is treated as the biosignal at the processing of the latter part of the main part 4 of the sleep state measuring apparatus when the sleep state is measured.

This biosignal sensor 5 is equipped with connection port 51, water chamber 52, pressure receiving membrane 53, air chamber 54, and pressure fluctuation detecting part 55 as shown in FIG. 2. The tube 3 (FIG. 1) is connected to the connection port 51, and the water chamber 52 is connected with the mattress 2. The pressure receiving membrane 53 divides the water chamber 52 and the air chamber 54. The water chamber 52 is also filled with water, and the water can flow through the tube 3 from the mattress 2 to the water chamber 52. The air chamber 54 is filled with air and the interior of the chamber is maintained at 1 atmosphere, for example.

The pressure fluctuation detecting part 55 is equipped at the surface of the pressure receiving membrane 53 on the side of the air chamber 54. The pressure fluctuation detecting part 55 has the Wheatstone bridge circuit where the strain gauge is incorporated, and the detecting part 55 is formed as an electric circuit as shown in FIG. 3 for example. That is, a resistance R1 among resistances R1 to R4 in the Wheatstone bridge circuit in FIG. 3 is equivalent to the strain gauge 55a of the pressure fluctuation detecting part 55. The strain gauge 55a is pasted on the surface of the pressure receiving membrane 53. The pressure fluctuation detecting part 55 amplifies the voltage between A and B in FIG. 3 by differential amplification circuit C1, and obtains this as a sensor output Vs.

The fluctuation of the pressure transmitted through the water passing the mattress 2, the tube 3, and the water chamber 52 in order vibrates the pressure receiving membrane 53 to the right and the left in FIG. 2, and expands and contracts up and down in FIG. 2. The strain gauge 55a of the pressure fluctuation detecting part 55 detects the pressure fluctuation, and the pressure fluctuation detecting part 55 outputs the pressure fluctuation detected as the biosignal to the variable amplifier 41 (below-mentioned FIG. 9) in the main part 4 of the sleep state measuring apparatus. FIG. 4 shows the example of the biosignal (sensor output Vs). In the biosignal shown here, the signal produced by the heartbeat of the user showing cycle T around 0.8 second is included. The respiration and other body motions other than the heartbeat appear in the biosignal, and these biosignals change depending on the user's sleep state (the sleep stage, the sleep quality) or the like.

In addition, the value of the mattress internal pressure showing the biosignal is the addition of the fluctuation part to the static component (an offset part) as already mentioned, and it is confirmed by experiment that the size of the static component of the mattress internal pressure influences the size of the fluctuation of the mattress internal pressure.

That is, in this experiment, as shown in FIG. 5(a), the mattress 62 is placed on the pedestal 61 and this mattress 62 is put between the pedestal 61 and the press board 63. One end of the arm 64 is attached to the press board 63, and the other end of the arm 64 is attached to one point on the disk 65. With the experimental apparatus, the press board 63 carries out reciprocating movement toward up-and-down direction with a constant period by rotating the disk 65 with constant angular velocity.

A similar sensor to the biosignal sensor 5 is equipped in the mattress 62. With the reciprocating movement of the press board 63, the load is applied on the mattress 62, and the output value of the sensor changes in the form similar to a sine wave form, as shown in the graph of FIG. 5(b).

Here, the amplitude M of the output wave of the sensor changes with the amount of water X in the mattress. The relation between the amount of water X in the mattress and the amplitude M is obtained by working the experimental apparatus and recording the amplitude M of the sensor output, making the amount of water X increasing from a comparatively small quantity gradually. When the experiment mentioned above is conducted with other plural mattresses 62 of the same specification, it is confirmed from the experimental results that the amount of the differences of the amplitude M of the plural mattresses 62 is very small.

The relation of the static component P of the mattress internal pressure (mattress internal pressure at the time of no weighting) and the fluctuation part ΔV of the mattress internal pressure shown in the graph of FIG. 6 will be obtained from the relation between the amount of water X in this mattress and the amplitude M of the output. That is, since the amount of water X in the mattress is approximately proportional to the static component P of the mattress internal pressure, the static component P of the mattress internal pressure of this FIG. 6 can be transposed with the amount X of water in the mattress. Also, since the amplitude M of the sensor output can be termed index showing the fluctuation part ΔV of the mattress internal pressure, the fluctuation part ΔV of the mattress internal pressure in FIG. 6 can be transposed with the amplitude M of the sensor output.

FIG. 7 and FIG. 8 show schematically the influence on the fluctuation part ΔV of the mattress internal pressure by the static component P of the mattress internal pressure. Then, when the static component of the mattress internal pressure is value $P_1$, the fluctuation part (the size of the amplitude of the mattress internal pressure) of the mattress internal pressure is supposed to be $\Delta V_1$. If the static component $P_1$ (FIG. 7(a)) of the mattress internal pressure is smaller than the static component $P_2$ (FIG. 8(a)) at the time, the fluctuation part $\Delta V_1$ (FIG. 7(b)) from the static component $P_1$ also has the relation of becoming smaller than the fluctuation part $\Delta V_2$ (FIG. 8(b)) from the static component $P_2$.

That is, when the static component P of the mattress internal pressure is larger, the pressure receiving membrane is tightly stretched. Therefore, according to the same principle of a drum, when the static component P of the mattress internal pressure is larger, the fluctuation part ΔV of the mattress internal pressure become larger.

However, such relation between the static component P of mattress internal pressure and the fluctuation part ΔV of the mattress internal pressure applies only in the case where the static component P of the mattress internal pressure is smaller than a certain value $P_0$ (FIG. 6) (only in case of $P<P_0$). That is, there is a limit of the expansion of the pressure receiving membrane, and the deformation of the pressure receiving membrane becomes hard beyond its expansion limit. Therefore, when the static component P of the mattress internal pressure becomes larger than the value $P_0$ ($P>P_0$), when the static component P of the mattress internal pressure becomes larger, the fluctuation part ΔV of the mattress internal pressure becomes smaller.

One of the characteristics of the present invention is that the amplification factor of the biosignal (the amplification factor A in the variable amplifier 41 in FIG. 9) is automatically set from the static component P, using such relation between the static component P of the mattress internal pressure and the fluctuation part ΔV. One of other characteristics of the present invention is that the same single biosignal sensor 5 detects both the biosignal and the static component P of the mattress internal pressure used for setting the amplification factor. Hereafter, the setting of the amplification factor of the biosignal will be explained in detail.

The main part 4 of the sleep state measuring apparatus has variable amplifier 41, filter 42, amplifier 43, analog to digital converter 44, and controller 45 in addition to the biosignal sensor 5 mentioned above, as shown in FIG. 9. The variable amplifier 41 amplifies the biosignal outputted by the biosignal sensor 5.

The filter 42 comprises three band pass filters (BPF) or the like. One of these three BPF extracts the signal corresponding to the heartbeat with frequency bands, such as 0.5 Hz to 2 Hz, from the biosignal outputted by the variable amplifier 41 as the heartbeat signal. One of other BPF extracts the signal corresponding to the respiration of a frequency band, such as 0.2 Hz to about 1 Hz, from the biosignal outputted by the variable amplifier 41 as the respiration signal. In addition, another of the BPF extracts the signal corresponding to other body motion more than 10 Hz frequency band from the biosignal outputted by the variable amplifier 41 as a body motion signal.

The amplifier 43 amplifies the heartbeat signal, the respiration signal, and the body motion signal extracted through the filter 42. A fixed value is used for the amplification factor for the amplifier 43. The analog to digital converter 44 carries out the analog to digital conversion of the heartbeat signal, the respiration signal, and the body motion signal outputted by the amplifier 43 for the processing in latter step controller 45.

The controller 45 is equipped with CPU, RAM, ROM, or the like, and estimates the user's sleep state by executing a predetermined program using the heartbeat signal, the respiration signal, and the body motion signal after the analog to digital conversions. To give an example for estimating the sleep state, the heart rate from the heartbeat signal is calculated, and the sleep stage (any one of non-REM sleep of stages 1 to 4 and REM sleep) can be judged by whether this calculated heart rate is in the scope of any value. Also, it is possible to calculate the breathing rate from the respiration signal and to count how many times the apnea of 10 seconds or more has generated during the sleep for 7 hours from the calculated breathing rate. The estimation of the sleep state in this controller 45 or the like is the art of common knowledge, and the details are disclosed by Japanese Unexamined Patent Application Publication No. 2004-113618, No. 2004-113329, or the like.

In addition, indicating part 46, input part 47, and auxiliary memory part 48 are connected to the controller 45. The indicating part 46 displays the estimation result of the user's sleep state. The input part 47 comprises the measurement beginning button which directs the beginning of the sleep state measurement, and the measuring finishing button which directs the finish of the sleep state measurement.

Also, the auxiliary memory part 48 comprises nonvolatile memory such as EEPROM, a hard disk drive, or the like, and the program which the controller 45 executes, the data used in the program, or the like are memorized in this auxiliary memory part 48. In particular, the reference table showing the correspondence relation between the static component P of the mattress internal pressure and the fluctuation part $\Delta V$ of the mattress internal pressure in FIG. 6 is stored in this auxiliary memory part 48. The controller 45 can specify the static component P of the mattress internal pressure, and can read the fluctuation part $\Delta V$ of the mattress internal pressure corresponding to the static component P.

As to setting the amplification factor A of the variable amplifier 41 in controller 45, it will be explained in detail in FIG. 10 and FIG. 11. FIG. 10 shows the flow of the sleep state measuring processing (sleep state measurement program) which controller 45 (CPU) executes immediately after pushing the measurement beginning button of the input part 47.

In Step 1 (a step is hereafter abbreviated to S) of the sleep state measuring processing, the controller 45 sets the amplification factor A of the variable amplifier 41 first. As to setting of the amplification factor A, it will be explained in following FIG. 11.

It is judged whether the measuring finish button of input part 47 was pushed down after setting the amplification factor A to the variable amplifier 41 (S2). When the measuring finish button is not pushed down (it is NO at S2), the biosignal is measured in S3. That is, the digital value of the heartbeat signal, the respiration signal and the body motion signal obtained through the analog to digital conversion by the analog to digital converter 44, are obtained every 0.05 second, for example, and is stored in the auxiliary memory part 48.

On the other hand, when the measuring finish button is pushed down (it is YES at S2), the result of the sleep state measuring is displayed in S4. That is, from the heartbeat signal, the respiration signal, and the body motion signal stored in the auxiliary memory part 48 at S3, the controller 45 judges the sleep stage, counts apnea, and displays the result on the indicating part 46, as described above. After indicating the measuring result, this processing finishes.

Then, in the setting processing of the amplification factor in FIG. 11 corresponding to the above S1, the controller 45 first obtains the static component P of the mattress internal pressure detected by the biosignal sensor 5 at S11. That is, in starting the sleep state measuring, the mattress 2 needs to be in the no-load state here. For example, in the indicating part 46, the indication "Under initialization. Please do not get on the mattress." is possible. By such indication, before the amplification factor is set, the user is guided not to get on the mattress 2.

The sensor output Vs of the biosignal sensor 5 in the no-load state is taken as the static component P of the mattress internal pressure. (The relation between the sensor output Vs and the mattress internal pressure is approximately linear.)

Then at S12, the controller 45 specifies the fluctuation part $\Delta V$ of the mattress internal pressure from the static component P of the mattress internal pressure obtained at S11. The value of the fluctuation part $\Delta V$ changes depending on the value of the static component P, and it is corresponded to the static component P by the experiment or the simulation performed beforehand. Concretely, the controller 45 reads out the fluctuation part $\Delta V_a$ depending on the detected static component $P_a$ from the reference table (FIG. 6) in the auxiliary memory part 48.

Then, the controller 45 corrects the predetermined standard amplification factor $A_0$ at S13 by using the fluctuation part $\Delta V$ of the mattress internal pressure specified at S12, and calculates the amplification factor A in the variable amplifier 41. To explain the calculation concretely, the static component P of the mattress internal pressure is subject to $P_0$ as a standard, and the fluctuation part $\Delta V$ of the mattress internal pressure in this case is subject to the standard fluctuation part $\Delta V_0$ (FIG. 6). Also, the standard amplification factor $A_0$ is subject to the amplification factor A in this case. (The auxiliary memory part 48 can store the standard fluctuation part $\Delta V_0$ and the standard amplification factor $A_0$.)

Then, the fluctuation part $\Delta V_a$ is obtained at S12, and the following numerical formula 1 gives the correction factor $K_a$ to the standard amplification factor $A_0$ from the fluctuation part $\Delta V_a$.

$$K_a = \Delta V_0 / \Delta V_a \qquad \text{[Numerical formula 1]}$$

That is, the correction factor $K_a$ is calculated by dividing the standard fluctuation part $\Delta V_0$ of the mattress internal pressure by the fluctuation part $\Delta V_a$ depending on the static component $P_a$ of the mattress internal pressure. By multiplying the standard amplification factor $A_0$ into the calculated correction factor $K_a$, the amplification factor $A_a$ in the variable amplifier 41 is calculated. The controller 45 sets this obtained amplification factor $A_a$ to the variable amplifier 41. Then, the return of this processing is carried out.

Immediately after the amplification factor setting processing, the controller 45 may perform the following indication to the indication part 46. That is, the indication is displayed as "Initialization has been completed. Please lie down on the mattress". And the indication guides the user to lie down on the mattress 2.

As described above, in the sleep state measuring apparatus, the size of the fluctuation part ΔV of the mattress internal pressure depending on the value is specified from the static component P of the detected mattress internal pressure. Then, the amplification factor A in the variable amplifier 41 is set by correcting the standard amplification factor $A_0$ based on the fluctuation part ΔV. Therefore, even if the mattress 2 suffers long-term deterioration and the expansion occurs at the mattress surface, even if the content of the mattress decreases, or even if the pressure in the static state of the fluid in the mattress by temperature, height or the like fluctuates, the suitable amplification factor of the biosignal can be set simply.

Also, the automatic-gain-control unit provided in the conventional apnea detecting apparatus consists of an additional circuit for exclusive use. Therefore, although there is no clear description in Japanese Unexamined Patent Application Publication No. 2000-271103, the sleep state measuring apparatus cannot but serve as complicated composition and operation by the additional circuit. Also, in the conventional apnea detecting apparatus, the absolute pressure and the microdifferential pressure (the biosignal) are generally measured by a separate sensor.

In contrast to these, the component part concerned with the setting of the amplification factor A of the variable amplifier 41 in the sleep state measuring apparatus of the present invention is comparably simple as shown in FIG. 9 to FIG. 11. In particular, the biosignal sensor 5 in the sleep state measuring apparatus has two functions. That is, one of these functions is the function of measuring the absolute pressure for setting the amplification factor A of the variable amplifier 41, and the other is the function of measuring the original biosignal. These two functions of the biosignal sensor 5 are greatly useful for the simplification of the composition of the whole apparatus.

Other Embodiments, or the Like

Although, as mentioned above, the present invention is explained with the concrete embodiment, the present invention is not limited to the above-mentioned embodiment, but can be changed and performed in the scope which does not deviate from the gist of the present invention.

A. In the above-mentioned embodiment, for example, the static component P of the mattress internal pressure was made the detected value of the mattress internal pressure in case of no-load. Unlike this, it is possible to obtain the static component P of the mattress internal pressure in the state where the user gets on the mattress.

That is, the static component P of the mattress internal pressure is taken from the fluctuating sensor output Vs of the biosignal sensor 5 in the state where the user gets on the mattress. Hereby, it is possible strictly to classify whether the user has got on the mattress or not, and to solve the problem of the timing where the control is necessary to be carried out corresponding to this classification.

Concretely, (a) the approach of putting through a low pass filter (LPF) against the sensor output Vs, and (b) the approach of taking the average of the sensor output Vs are cited. In the approach using the LPF in (a), this LPF can be equipped as the 4th filter that forms filter 42 (FIG. 9). The LPF transmits the low frequency band, for example, the biosignal of 0.2 Hz or less, to the latter step. This biosignal that passes through the LPF is detected as the static component P of the mattress internal pressure, is inputted into the controller 45, and the amplification factor setting processing in FIG. 11 is performed based on this static component P.

In the approach of taking the average value in (b), the biosignal outputted by the biosignal sensor 5 and amplified by the variable amplifier 41 (FIG. 9) may be made to be inputted into the controller 45 via the amplifier 43 and the analog to digital converter 44 suitably. In the controller 45, the average value of this biosignal is calculated, and the calculated average value is used as the static component P of the mattress internal pressure, then the amplification factor setting processing in FIG. 11 is performed.

B. In the above-mentioned embodiment, the specification of the fluctuation part ΔV of the mattress internal pressure depending on the static component P of the mattress internal pressure shall be based on the reference table where these correspondence relations are described. Unlike this, without using the reference table, the correspondence relation such as the graph in FIG. 6 as the calculating formula may be indicated and the fluctuation part ΔV of the mattress internal pressure may be calculated by substituting the static component P of the mattress internal pressure into the calculating formula.

C. In the above-mentioned embodiment, although the strain gauge 55a (FIG. 3) is described to be used for the biosignal sensor, a semiconductor strain gauge may also be used. In order to improve the accuracy of the detection value of the mattress internal pressure, a plurality of strain gauges may be made to stick on pressure receiving membrane 53 in the biosignal sensor 5, or to use a plurality of biosignal sensors 5, of course.

D. In the above-mentioned embodiment, by one biosignal sensor 5, while detecting the static component P of the mattress internal pressure before the sleep state measurement beginning, the biosignal (the mattress internal pressure) shall be detected at the time of sleep state measuring. Unlike this, the both of the biosignal sensor which measures the static component P of the mattress internal pressure, and the microphone sensor used conventionally may be used. That is, it is possible that the microphone sensor is made to detect the original biosignal, and the biosignal sensor is made to be used only for setting the amplification factor as to the detecting value with the microphone sensor.

E. The strain gauge 55a may be made to stick on the position directly where it corresponds to the upper surface or the undersurface of the mattress 2, for example, corresponding to the lower position near the center of the body of the human being. In this case, the tube 3 becomes unnecessary, and the composition of the biosignal sensor and the sleep state measuring apparatus will become simpler.

F. In the above-mentioned embodiment, the reference table shall show the correspondence relation between the static component P of the mattress internal pressure P and the fluctuation part ΔV. Replacing this, the reference table may show the correspondence relation between the static component P of the mattress internal pressure and the correction factor K. In this case, the calculation with said numerical formula I will be performed beforehand and the calculation result will be stored in the reference table.

G. Of course, the standard value $P_0$ for the static component P of the mattress internal pressure may not use the value of the extremum as shown in FIG. 6.

What is claimed is:

1. A sleep state measuring apparatus for detecting a biosignal which changes depending on a sleep state of a living body that gets on a mattress filled with a fluid, amplifying the biosignal, and estimating the sleep state based on the amplified biosignal, comprising:

a detector which detects a static component P of a mattress internal pressure which is a pressure of the fluid in the mattress;

a specifier which specifies a fluctuation part $\Delta V$ of the mattress internal pressure at a time of applying a predetermined, non-zero load which changes depending on the static component P from the static component P detected by the detector using a corresponded relation performed beforehand between the static component P of the mattress internal pressure and the fluctuation part $\Delta V$ of the mattress internal pressure; and an electronic calculator comprising a processor which is programmed with an algorithm to calculate an amplification factor A for input into a variable amplifier and used for amplification of the biosignal by correcting a predetermined standard amplification factor $A_0$ with the fluctuation part $\Delta V$ specified by the specifier, wherein the detector detects the matress internal pressure which fluctuates in a state where the living body gets on the matress as the biosignal.

2. The sleep state measuring apparatus according to claim 1, wherein:

the sleep state measuring apparatus is equipped with a memorizer for memorizing a reference table showing correspondence relation between the static component P of the mattress internal pressure and the fluctuation part $\Delta V$ of the mattress internal pressure;

the specifier obtains the fluctuation part $\Delta V$ depending on the static component P detected by the detector from the reference table memorized in the memorizer.

3. The sleep state measuring apparatus according to claim 1, wherein:

the calculator calculates a correcting factor by dividing a standard fluctuation part $\Delta V_0$ which is the fluctuation part of the mattress internal pressure corresponding to the standard amplification factor $A_0$ by the fluctuation part $\Delta V$ specified by the specifier; and calculates the amplification factor A by multiplying the standard amplification factor $A_0$ by the calculated correcting factor.

4. The sleep state measuring apparatus according to claim 1, wherein:

the detector detects the detected value in a state where the living body does not get on the mattress as the static component P of the mattress internal pressure.

5. The sleep state measuring apparatus according to claim 1, wherein:

the sleep state measuring apparatus is equipped with a low pass filter which transmits a low frequency band of the biosignal;

the detector detects the biosignal which has passed the low pass filter in a state where the living body gets on the mattress as the static component P of the mattress internal pressure.

6. The sleep state measuring apparatus according to claim 1, wherein:

the detector calculates an average of the biosignal in a state where the living body gets on the mattress; and the detector detects the calculated average as the static component P of the mattress internal pressure.

7. The sleep state measuring apparatus according to claim 1, wherein the detector comprises:

a fluid chamber filled with fluid which is connected with the mattress, an air chamber filled with air, a pressure receiving membrane which separates the air chamber from the fluid chamber, and a strain gauge which is set on the pressure receiving membrane and detects the fluctuation of a fluid pressure in the fluid chamber.

8. A sleep state measuring method for detecting a biosignal which changes depending on a sleep state of a living body that gets on a mattress filled with a fluid, amplifying the biosignal, and estimating the sleep state based on the amplified biosignal, comprising the steps of:

detecting a static component P of a mattress internal pressure which is a pressure of the fluid in the mattress;

specifying a fluctuation part $\Delta V$ of the mattress internal pressure at a time of applying a predetermined, non-zero load which changes depending on the static component P from the static component P detected in the step of detecting using a corresponded relation performed beforehand between the static component P of the mattress internal pressure and the fluctuation part $\Delta V$ of the mattress internal pressure;

using an algorithm to calculate an amplification factor A by correcting a predetermined standard amplification factor $A_0$ with the fluctuation part $\Delta V$ specified in the step of specifying; and setting the amplification factor A of a variable amplifier for amplification of the biosignal, wherein in the step of detecting a detector detects the mattress internal pressure which fluctuates in a state where the living body gets on the mattress as the biosignal.

* * * * *